United States Patent [19]

Taguchi et al.

[11] Patent Number: 5,041,462
[45] Date of Patent: Aug. 20, 1991

[54] NOVEL SUBSTITUTED ACETAMIDE COMPOUNDS AND USE AS ANTI-ALLERGIC AGENTS

[75] Inventors: Hiroaki Taguchi, Ibaraki; Takeo Katsushima, Kyoto; Masakazu Ban, Mukoh; Mitsuru Takahashi; Kiyotaka Shinoda, both of Otsu; Akihiko Watanabe, Otsu, all of Japan

[73] Assignee: Toyo Boseki Kabushiki Kaisha, Osaka, Japan

[21] Appl. No.: 476,515

[22] Filed: Feb. 7, 1990

[30] Foreign Application Priority Data
Feb. 9, 1989 [JP] Japan .................. 1-30384

[51] Int. Cl.$^5$ ............... A61K 31/275; A61K 31/165; C07C 255/50; C07C 233/16
[52] U.S. Cl. ......................... 514/522; 558/414; 558/417; 560/251; 564/153; 564/155; 564/157; 514/546; 514/552; 514/616; 514/329; 514/238.2; 544/163; 544/164
[58] Field of Search .............. 558/414, 417; 560/251; 564/153, 155, 157; 514/522, 546, 552, 616

[56] References Cited
U.S. PATENT DOCUMENTS
3,867,437 2/1975 Fujimura ..................... 544/106

FOREIGN PATENT DOCUMENTS
0315112 5/1989 European Pat. Off. .
1553299 9/1979 United Kingdom .

Primary Examiner—Johann Richter
Attorney, Agent, or Firm—Wegner, Cantor, Mueller & Player

[57] ABSTRACT

Novel substituted acetamide compounds of the formula

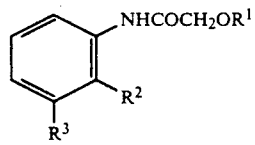

(I)

wherein $R^1$ is hydrogen atom, a lower alkyl group, a lower acyl group, or an aryl group; $R^2$ is cyano group or aminocarbonyl group; $R^3$ is a halogen atom, nitro group, a lower alkoxy group, a group of the formula: —$NR^4R^5$ (wherein $R^4$ is hydrogen atom, a lower alkyl group or a group of the formula: —$COCH_2OR^1$; $R^5$ is hydrogen atom or a lower alkyl group), or a cyclic amino group of the formula:

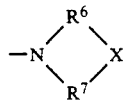

(wherein $R^6$ and $R^7$ are each an alkylene group having 1 to 3 carbon atoms, and X is oxygen atom or methylene), or a pharmaceutically acceptable acid addition salt thereof, which have excellent anti-allergic activity and are useful for the prophylaxis and treatment of various allergic diseases, and a pharmaceutical composition containing the amide compound as set forth above as an active ingredient.

5 Claims, No Drawings

NOVEL SUBSTITUTED ACETAMIDE COMPOUNDS AND USE AS ANTI-ALLERGIC AGENTS

This invention relates to novel substituted acetamide compounds having an anti-allergic activity and being useful as an anti-allergic agent. More particularly, it relates to substituted acetamide compounds of the formula:

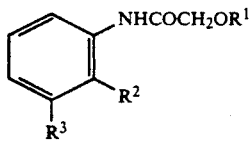

wherein $R^1$ is a hydrogen atom, a lower alkyl group, a lower acyl group, or an aryl group; $R^2$ is a cyano group or aminocarbonyl group; $R^3$ is a halogen atom, nitro group, a lower alkoxy group, a group of the formula: $-NR^4R^5$ (wherein $R^4$ is hydrogen atom, a lower alkyl group or a group of the formula: $-COCH_2OR^1$; $R^5$ is a hydrogen atom or a lower alkyl group), or a cyclic amino group of the formula:

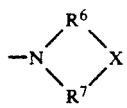

(wherein $R^6$ and $R^7$ are each an alkylene group having 1 to 3 carbon atoms, and X is a oxygen atom or methylene), or a pharmaceutically acceptable acid addition salt thereof.

PRIOR ART

There have hitherto been studied various compounds useful for prophylaxis and treatment of various kinds of allergic symptoms. Known compounds having an anti-allergic activity are, for example, Tranilast [i.e. N-(3,4-dimethoxycinnamoyl)anthranilic acid] (cf. The Journal of Allergy and Clinical Immunology, Vol. 57, No. 5, page 396, 1976) and Lodoxamide Ethyl [i.e. diethyl N,N'-(2-chloro-5-cyano-m-phenylene)dioxamate] (cf. Agents and Actions, Vol. 1, page 235, 1979). However, known anti-allergic agents are not necessarily satisfactory for the treatment of various kinds of allergic diseases, particularly the treatment of bronchial asthma.

BRIEF DESCRIPTION OF THE INVENTION

The present inventors have intensively studied many kinds of compounds and the pharmacological activities thereof in order to find a compound having excellent anti-allergic activity and have found that some specific substituted acetamide compounds show excellent anti-allergic activity.

An object of the invention is to provide novel substituted acetamide compounds having excellent antiallergic activity against various kinds of allergic diseases. Another object of the invention is to provide a pharmaceutical composition containing said substituted acetamide compounds as an active ingredient which is useful for the prophylaxis and treatment of various allergic diseases. Another object of the invention is to provide a process for preparing the substituted acetamide compounds and a pharmaceutical composition thereof. These and other objects and advantages of the invention will be apparent to those skilled in the art from the following description.

DETAILED DESCRIPTION OF THE INVENTION

The substituted acetamide compounds of this invention are the compounds of the formula (I) as set forth hereinbefore.

In the formula (I), the lower alkyl group for $R^1$ includes alkyl groups having 1 to 6 carbon atoms, for example, methyl or ethyl group. The lower acyl group for $R^1$ includes acyl groups having 1 to 6 carbon atoms, for example, acetyl or propionyl group. The aryl group for $R^1$ includes, for example, phenyl group. The halogen atom for $R^3$ includes fluorine, chlorine, bromine and iodine atom, preferably chlorine atom. The lower alkoxy group for $R^3$ includes alkoxy groups having 1 to 6 carbon atoms, for example, methoxy group. The lower alkyl group for $R^4$ and $R^5$ includes alkyl groups having 1 to 6 carbon atoms, for example, methyl or ethyl group. The compounds of the formula (I) wherein $R^3$ is amino group, a lower alkylamino group, a di(-lower)alkylamino group or and a cyclic amino group can form an acid addition salt with a pharmaceutically acceptable acid, and this invention includes also such acid addition salts.

The acid addition salts include inorganic acid addition salts such as hydrochloride, hydrobromide, hydroiodide, sulfate, phosphate, nitrate, etc., and organic acid addition salts such a acetate, lactate, tartrate, citrate, fumarate, maleate, methanesulfonate, ethanesulfonate, benzenesulfonate, toluenesulfonate, and other ionic acid salts.

Preferred compounds of this invention are the substituted acetamide compounds of the formula (I) wherein $R^1$ is hydrogen atom, an alkyl group having 1 to 6 carbon atoms, an acyl group having 1 to 6 carbon atoms; $R^2$ is cyano group or aminocarbonyl group; $R^3$ is halogen atom, nitro group, an alkoxy group having 1 to 6 carbon atoms, a group of the formula: $-NR^4R^5$ (wherein $R^4$ is hydrogen atom, an alkyl group having 1 to 6 carbon atoms, a hydroxyacetyl group, an acyloxyacetyl group, an alkoxyacetyl group; and $R^5$ is hydrogen atom or an alkyl group having 1 to 6 carbon atoms), or a cyclic amino group.

More preferred compounds are the substituted acetamide compounds of the formula (I) wherein $R^1$ is hydrogen atom, methyl, ethyl, acetyl, or propionyl; $R^2$ is cyano group or aminocarbonyl group; $R^3$ is chlorine atom, methoxy group, mono- or dimethylamino group, mono- or diethylamino group, hydroxyacetylamino group, acetoxyacetylamino group, piperidino group, or morpholino group.

Specifically preferred compounds are the following compounds:
2-(Acetoxyacetylamino)-6-(ethylamino)benzonitrile
2-(Ethylamino)-6-(methoxyacetylamino)benzonitrile
2-(Methoxyacetylamino)-6-(methylamino)benzonitrile
2-(Acetoxyacetylamino)-6-(methylamino)benzonitrile
2-(Ethoxyacetylamino)-6-(methylamino)benzonitrile
2-(Ethoxyacetylamino)-6-(ethylamino)benzonitrile
2-(Acetoxyacetylamino)-6-(N-acetoxyacetyl-N-methylamino)benzonitrile
2-(Methylamino)-6-(phenoxyacetylamino)benzonitrile
2-(Acetoxyacetylamino)-6-(ethylamino)benzamide
2-(Acetoxyacetylamino)-6-(methylamino)benzamide 2-(Ethylamino)-6-(propionyloxyacetylamino)benzonitrile
2-(Acetoxyacetylamino)-6-methoxybenzamide
2-(Acetoxyacetylamino)-6-methoxybenzonitrile
2-(Hydroxyacetylamino)-6-(methylamino)benzonitrile
2-(Ethylamino)-6-(hydroxyacetylamino)benzonitrile
2-(Acetoxyacetylamino)-6-nitrobenzonitrile
2,6-Bis(acetoxyacetylamino)benzonitrile
2-(Acetoxyacetylamino)-6-chlorobenzonitrile
2-(Acetoxyacetylamino)-6-aminobenzamide
2-(Acetoxyacetylamino)-6-(diethylamino)benzonitrile
2-(Acetoxyacetylamino)-6-piperidinobenzonitrile
2-(Acetoxyacetylamino)-6-(N-ethyl-N-methylamino)-benzonitrile
2-(Hydroxyacetylamino)-6-piperidinobenzonitrile
2-(Acetoxyacetylamino)-6-morpholinobenzonitrile
2,6-Bis(hydroxyacetylamino)benzonitrile
2-(Hydroxyacetylamino)-6-methoxybenzonitrile
2-(Hydroxyacetylamino)-6-morpholinobenzonitrile.

The substituted acetamide compounds (I) of this invention can be prepared, for example, by the following process, which comprises reacting an amino compound of the formula:

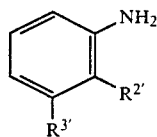

wherein $R^{2'}$ is cyano group or aminocarbonyl group; and $R^{3'}$ is halogen atom, nitro group, a lower alkoxy group, a group of the formula: $—NR^{4'}R^{5'}$ ($R^{4'}$ and $R^{5'}$ are each hydrogen atom or a lower alkyl group), or a group of the formula:

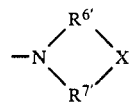

(wherein $R^{6'}$ and $R^{7'}$ are an alkylene group having 1 to 3 carbon atoms, and X is oxygen atom or methylene group), with an acid halide of the formula:

$$R^{1'}OCH_2CO—hal \quad (III)$$

wherein $R^{1'}$ is a lower alkyl group, a lower acyl group, or an aryl group, and hal is a halogen atom (e.g. chlorine atom).

The above reaction can be carried out in an appropriate solvent (e.g. pyridine, chloroform, dichloromethane, N,N-dimethylformamide, etc.) in the presence of a base (e.g. pyridine, triethylamine, etc.). The reaction proceeds without heating, but may be carried out with heating in order to complete the reaction. The reaction may also be carried out in the presence of an aqueous alkali solution like in Schotten Baumann reaction.

In the case of the compounds of the formula (I) wherein $R^1$ is a lower acyl group, the obtained compounds may optionally be hydrolyzed to obtain the compounds of the formula (I) wherein $R^1$ is hydrogen atom. In the case of the compounds of the formula (I) wherein $R^2$ is cyano group, the compounds may optionally be subjected to hydrolysis to be converted into the corresponding compounds (I) wherein $R^2$ is aminocarbonyl group. In the case of the compounds of the formula (I) wherein $R^3$ is nitro group, the compounds may optionally be subjected to reduction to obtain the corresponding compounds (I) wherein $R^3$ is amino group. Besides, the compounds of the formula (I) wherein $R^3$ is amino group, a lower alkylamino group, di(lower)alkylamino group, or a cyclic amino group may optionally be converted into an acid addition salt thereof by treating them with an inorganic acid or organic acid in a usual manner.

The compounds of this invention have potent inhibitory activity against immediate allergic reaction and hence are useful for the prophylaxis and treatment of immediate allergy, such as bronchial asthma, urticaria, allergic rhinitis, etc.

The anti-allergic activity of the compounds of this invention is illustrated by the following experiment.

Experiment

Male Wistar rats (weighing about 200 g) were passively sensitized by intradermal injection of each 0.1 ml of a solution of rat antiserum to egg albumin in each of two sites (totally four sites) at both sides of dorsal median line. After 48 hours, each rat was challenged by injecting a mixture (1 ml) of egg albumin and Evans blue solution via tail vein to induce passive cutaneous anaphylaxis (PCA). 30 minutes after the challenge, the rats were sacrificed to take the blueing region, and the amount of pigment from the blueing region was measured by the method of Katayama et al. (cf. Microbiol. Immunol., Vol. 22, page 89, 1978). Test compounds were orally administered to the rats (each 3 rats) in a dose of 30 mg/kg 30 minutes before the antigen challenge. The PCA inhibitory rate of the compounds of this invention is shown in Table 1.

TABLE 1

| Test compounds | PCA inhibitory rate (%) |
|---|---|
| 2-(Acetoxyacetylamino)-6-(ethylamino)-benzonitrile (compound in Example 1) | 95 |
| 2-(Methoxyacetylamino)-6-(methylamino)-benzonitrile (compound in Example 3) | 91 |
| 2-(Ethylamino)-6-(propionyloxyacetylamino)-benzonitrile (compound in Example 11) | 96 |
| 2-(Acetoxyacetylamino)-6-methoxybenzamide (compound in Example 12) | 79 |
| 2-(Ethylamino)-6-(hydroxyacetylamino)-benzonitrile (compound in Example 15) | 93 |
| 2,6-Bis(acetoxyacetylamino)benzonitrile (compound in Example 17) | 73 |
| 2-(Acetoxyacetylamino)-6-(diethylamino)-benzonitrile (compound in Example 20) | 97 |
| 2-(Acetoxyacetylamino)-6-morpholino-benzonitrile (compound in Example 24) | 98 |

The compounds of this invention can be administered by oral or parenteral route, preferably by oral route. Alternatively, the compounds may be administered by inhalation in the form of aerosol spray or with an inhalator in the form of dry powder so that the compound can make contact directly with the lung.

The clinical dose of the compounds of this invention may vary according to the kinds of the compounds, administration routes, severity of diseases, age, sex and body weight of patients, or the like, but is usually in the range of 2 to 2,000 mg per day in the human. The dose may be divided and administered in two to several times per day.

The compounds of this invention are usually administered to patients in the form of a pharmaceutical composition which contains a non-toxic and effective amount of the compounds. The pharmaceutical composition is in the dosage form of tablets, capsules, granules, syrups, powders, and the like for oral administration, and for the parenteral administration, they are in the form of aqueous solutions for intravenous injection, or oil suspension for intramuscular injection. The pharmaceutical composition is usually prepared by admixing the active compound of the formula (I) or a pharmaceutically acceptable acid addition salt thereof with conventional pharmaceutical carriers or diluents. Suitable examples of the carriers and diluents are lactose, glucose, dextrin, starch, sucrose, microcrystalline cellulose, sodium carboxymethylcellulose, calcium carboxymethylcellulose, gelatin, hydroxypropylcellulose, polyvinylpyrrolidone, magnesium stearate, talc, carboxyvinyl polymer, sorbitan fatty acid esters, sodium lauryl sulfate, macrogol, vegetable oils, wax, liquid paraffin, white petrolatum, propylene glycol, water, or the like.

This invention is illustrated by the following Examples but should not be construed to be limited thereto.

EXAMPLE 1

Preparation of 2-(acetoxyacetylamino)-6-(ethylamino)benzonitrile:

To a solution of 2-amino-6-(ethylamino)benzonitrile (6.7 g) in methylene chloride (100 ml) is added pyridine (4.8 ml), and to the mixture is added dropwise acetoxyacetyl chloride (6.5 ml) which is cooled in an ice bath. The mixture is stirred at room temperature for 1 hour, and thereafter, water is added thereto, and the mixture is extracted with methylene chloride. The organic layer is dried over anhydrous sodium sulfate and the solvent is distilled off under reduced pressure. The resulting crude crystals are recrystallized from ethyl acetate-hexane to give the title compound (7.8 g) having the following physical properties.

Melting point: 110°-113° C.

IR (KBr) $\upsilon$: 3455, 3365, 3285, 2215, 1775, 1690, 1615, 1580, 1555, 1515, 1480, 1415, 1330, 1290, 1210, 1160, 1090, 970, 840, 790 cm$^{-1}$ NMR (DMSO-$d_6$) $\delta$: 9.69 (1 H, brs), 7.19–6.42 (3 H, m), 5.77 (1 H, m), 4.52 (2 H, s), 3.14 (2 H, m), 2.02 (3 H, s), 1.08 (3 H, t)

Elementary analysis:
Calcd. (%): C,59.76; H,5.79; N,16.08;
Found (%): C,59.79; H,5.79; N,16.07.

EXAMPLE 2

Preparation of 2-(ethylamino)-6-(methoxyacetylamino)benzonitrile:

To a solution of 2-amino-6-(ethylamino)benzonitrile (3.4 g) in methylene chloride (50 ml) is added pyridine (2.4 ml), and thereto is added dropwise methoxyacetyl chloride (2.8 ml) which is cooled in an ice bath. The mixture is stirred at room temperature for 1 hour, and thereafter, water is added thereto, and the mixture is extracted with methylene chloride. The organic layer is dried over anhydrous sodium sulfate, and the solvent is distilled off under reduced pressure. The resulting crude crystals are recrystallized from ethyl acetate-hexane to give the title compound (3.2 g) having the following physical properties.

Melting point: 118°-119° C.

IR (KBr) $\upsilon$: 3370, 3350, 3130, 2975, 2935, 2195, 1715, 1610, 1585, 1550, 1510, 1480, 1420, 1325, 1255, 1200, 1115, 1080, 990, 790, 675 cm$^{-1}$.

NMR (DMSO-$d_6$) $\delta$: 9.31 (1 H, brs), 7.23–6.45 (3 H, m), 5.86 (1 H, brt), 3.94 (2 H, s), 3.34 (3 H, s), 3.14 (2 H, m), 1.13 (3 H, t).

Elementary analysis:
Calcd. (%): C,61.79; H,6.48; N,18.01;
Found (%): C,61.95; H,6.49; N,17.99.

EXAMPLE 3

Preparation of 2-(methoxyacetylamino)-6-(methylamino)benzonitrile:

To a solution of 2-amino-6-(methylamino)benzonitrile (3.3 g) in methylene chloride (50 ml) is added pyridine (3.6 ml) and thereto is added dropwise methoxyacetyl chloride (4.2 ml) which is cooled in an ice bath. The mixture is stirred at room temperature for 1 hour, and thereafter, water is added thereto, and the mixture is extracted with methylene chloride. The organic layer is dried over anhydrous sodium sulfate, and the solvent is distilled off under reduced pressure. The resulting crude crystals are recrystallized from ethyl acetate-hexane to give the title compound (1.9 g) having the following physical properties.

Melting point: 109°-111° C.

IR (KBr) $\upsilon$: 3385, 2955, 2825, 2205, 1705, 1615, 1585, 1555, 1510, 1440, 1420, 1380, 1340, 1310, 1205, 1170, 1120, 990, 790, 685 cm$^{-1}$.

NMR (DMSO-$d_6$) $\delta$: 9.42 (1 H, brs), 7.45–6.41 (3 H, m), 6.12 (1 H, m), 4.02 (2 H, s), 3.45 (3 H, s), 2.75 (3 H, d).

Elementary analysis:
Calcd. (%): C,60.26; H,5.98; N,19.17;
Found (%): C,60.09; H,5.93; N,19.46

EXAMPLE 4

Preparation of 2-(acetoxyacetylamino)-6-(methylamino)benzonitrile:

To a solution of 2-amino-6-(methylamino)benzonitrile (4.4 g) in methylene chloride (50 ml) is added pyridine (4.9 ml), and thereto is added dropwise acetoxyacetyl chloride (6.5 ml) which is cooled in an ice bath. The mixture is stirred at room temperature for 1 hour, and thereafter, water is added thereto, and the mixture is extracted with methylene chloride. The organic layer is dried over anhydrous sodium sulfate, and the solvent is distilled off under reduced pressure. The resulting crude crystals are recrystallized from ethyl acetate-hexane to give the title compound (5.1 g) having the following physical properties.

Melting point: 144°-145° C.

IR (KBr) $\upsilon$: 3435, 3205, 2195, 1755, 1680, 1615, 1555, 1515, 1485, 1420, 1290, 1270, 1240, 1215, 1175, 1065, 785 cm$^{-1}$.

NMR (DMSO-$d_6$) $\delta$: 9.82 (1 H, brs), 7.34–6.46 (3 H, m), 6.06 (1 H, brq), 4.64 (2 H, s), 2.74 (3 H, d), 2.09 (3 H, s)

Elementary analysis:
Calcd. (%): C,58.29; H,5.30; N,16.99;
Found (%): C,58.21; H,5.28; N,17.08.

EXAMPLE 5

Preparation of 2-(ethoxyacetylamino)-6-(methylamino)benzonitrile:

To a solution of 2-amino-6-(methylamino)benzonitrile (3.3 g) in methylene chloride (50 ml) is added pyridine (3.9 ml), and thereto is added dropwise ethoxyacetyl chloride (5 ml) which is cooled in an ice bath. The mixture is stirred at room temperature for 1 hour, and thereafter, water is added thereto, and the mixture is extracted with methylene chloride. The organic layer is dried over anhydrous sodium sulfate, and the solvent is distilled off under reduced pressure The resulting crude crystals are recrystallized from ethyl acetate-hexane to give the title compound (3.2 g) having the following physical properties.

Melting point 133° –134° C.

IR (KBr) $\nu$: 3405, 3365, 2980, 2895, 2185, 1715, 1615, 1585, 1555, 1515, 1490, 1440, 1420, 1310, 1170, 1125, 785, 670 cm$^{-1}$.

NMR (DMSO-$d_6$) $\delta$: 9.32 (1 H, brs), 7.42–6.36 (3 H, m), 6.16 (1 H, m), 4.03 (2 H, s), 3.48 (2 H, q), 2.25 (3 H, d), 1.22 (3 H, t).

Elementary analysis:
Calcd. (%): C,61.79; H,6.48; N,18.01;
Found (%): C,61.71; H,6.37; N,18.04.

EXAMPLE 6

Preparation of 2-(ethoxyacetylamino)-6-(ethylamino)benzonitrile:

To a solution of 2-amino-6-(ethylamino)benzonitrile (4 g) in methylene chloride (100 ml) is added pyridine (2.8 ml), and thereto is added dropwise ethoxyacetyl chloride (3.9 ml) which is cooled in an ice bath. The mixture is stirred at room temperature for 1 hour, and thereafter, water is added thereto, and the mixture is extracted with methylene chloride. The organic layer is dried over anhydrous sodium sulfate, and the solvent is distilled off under reduced pressure. The resulting crude crystals are recrystallized from ethyl acetate-hexane to give the title compound (4.1 g) having the following physical properties.

Melting point: 84° –87° C.

IR (KBr) $\nu$: 3395, 3365, 2985, 2900, 2205, 1715, 1610, 1580, 1550, 1510, 1485, 1420, 1320, 1290, 1195, 1160, 1120, 1158, 900, 790, 670 cm$^{-1}$.

NMR (DMSO-$d_6$) $\delta$: 9.32 (1 H, brs), 7.45–6.42 (3 H, m), 5.97 (1 H, brt), 4.03 (2 H, s), 3.58 (3 H, q), 3.17 (2 H, m), 1.22 (3 H, t), 1.15 (3 H, t), Elementary analysis:
Calcd. (%): C,63.14; H,6.93; N,16.99;
Found (%): C,63.10; H,6.98; N,16.97.

EXAMPLE 7

Preparation of 2-(acetoxyacetylamino)-6-(N-acetoxyacetyl-N-methylamino)benzonitrle:

To a solution of 2-amino-6-(methylamino)benzonitrile (4.4 g) in methylene chloride (50 ml) is added pyridine (6.5 ml), and thereto is added dropwise acetoxyacetyl chloride (8.6 ml) which is cooled in an ice bath. The mixture is stirred at room temperature for 10 hours, and thereafter, water is added thereto, and the mixture is extracted with methylene chloride. The organic layer is dried over anhydrous sodium sulfate, and the solvent is distilled off under reduced pressure. The resulting crude crystals are recrystallized from ethanol to give the title compound (4.1 g) having the following physical properties.

Melting point: 124° –125° C.

IR (KBr) $\nu$: 3200, 3005, 2955. 2230, 1760, 1695, 1665, 1595, 1520, 1450, 1290, 1225, 1070, 825, 760 cm$^{-1}$.

NMR (DMSO-$d_6$) $\delta$: 9.70 (1 H, brs), 7.11 (3 H, m), 4.72 (2 H, s), 4.30 (2 H, brs), 3.16 (3 H, s), 2.10 (3 H, s), 1.99 (3 H, s)

Elementary analysis:
Calcd. (%): C,55.33; H,4.93; N,12.10;
Found (%): C,55.34; H,4.94; N,12.09.

EXAMPLE 8

Preparation of 2-(methylamino)-6-(phenoxyacetylamino)benzonitrile:

To a solution of 2-amino-6-(methylamino)benzonitrile (3.3 g) in methylene chloride (50 ml) is added pyridine (3.6 ml), and thereto is added dropwise phenoxyacetyl chloride (6.2 ml) which is cooled in an ice bath. The mixture is stirred at room temperature for 1 hour, and thereafter, water is added thereto, and the mixture is extracted with methylene chloride. The organic layer is dried over anhydrous sodium sulfate, and the solvent is distilled off under reduced pressure. The resulting crude crystals are recrystallized from ethanol to give the title compound (1.4 g) having the following physical properties.

Melting point: 201° –202° C.

IR (KBr) $\nu$: 3415, 2940, 2195, 2710, 2620, 1560, 1555, 1520, 1500, 1490, 1440, 1305, 1255, 1190, 1085, 1070, 845, 780, 755, 650 cm$^{-1}$.

NMR (DMSO-$d_6$) $\delta$: 9.76 (1 H, brs), 7.15 (6 H, m), 6.48 (1 H, d), 6.12 (1 H, brq), 4.68 (2 H, s), 2.74 (3 H, d).

Elementary analysis:
Calcd. (%): C,68.31; H,5.37; N,14.94;
Found (%): C,68.20; H,5.38; N,14.86.

EXAMPLE 9

Preparation of 2-(acetoxyacetylamino)-6-(ethylamino)benzamide:

To a solution of 2-amino-6-(ethylamino)benzamide (3 g) in methylene chloride (100 ml) is added pyridine (3 ml), and thereto is added dropwise acetoxyacetyl chloride (2.0 ml) which is cooled in an ice bath. The mixture is stirred at room temperature for 1 hour, and thereafter, the solvent is distilled off under reduced pressure. The resulting crude crystals are washed with water and ether and then are recrystallized from ethanol to give the title compound (2.5 g) having the following physical properties.

Melting point: 162° –163° C.

IR (KBr) $\nu$: 3445, 3405, 3305, 3205, 2975, 1760, 1670, 1610, 1545, 1500, 1470, 1380, 1325, 1225, 1160, 1120, 1085, 965, 775, 575 cm$^{-1}$.

NMR (DMSO-$d_6$) $\delta$: 9.72 (1 H, brs), 7.66 (2 H, brs), 7.11 (2 H, m), 6.42 (1 H, m), 5.43 (1 H, brt), 4.5 (2 H, s), 3.02 (2 H, m), 2.13 (3 H, s), 1.13 (3 H, t).

Elementary analysis:
Calcd. (%): C,55.91; H,6.13; N,15.05;
Found (%): C,55.74; H,6.16; N,14.97.

EXAMPLE 10

Preparation of 2-(acetoxyacetylamino)-6-(methylamino)benzamide:

To a solution of 2-amino-6-(methylamino)benzamide (3.6 g) in methylene chloride (100 ml) is added pyridine (4.8 ml), and thereto is added dropwise acetoxyacetyl chloride (3.2 ml) which is cooled in an ice bath. The mixture is stirred at room temperature for 1 hour, and thereafter, the solvent is distilled off under reduced pressure. The resulting crude crystals are washed with water and ether and then are recrystallized from ethanol to give the title compound (4.2 g) having the following physical properties.

Melting point: gradually decomposed from 100° C.

IR (KBr) $\nu$: 3475, 3425, 3310, 1735, 1680, 1645, 1615, 1500, 1475, 1435, 1245, 1170, 1070, 805 cm$^{-1}$.

NMR (DMSO-d$_6$) δ: 9.64 (1 H, brs), 7.58 (2 H, brs), 7.06–6.31 (3 H, m), 5.50 (1 H, brq), 4.50 (2 H, s), 2.66 (3 H, d), 2.09 (3 H, s).

Elementary analysis:
Calcd. (%): C,54.33; H,5.70; N,15.87;
Found (%): C,54.12; H,5.68; N,15.76.

EXAMPLE 11

Preparation of 2-(ethylamino)-6-(propionyloxyacetylamino)benzonitrile:

To a solution of 2-amino-6-(ethylamino)benzonitrile (2.3 g) in methylene chloride (50 ml) is added pyridine (1.6 ml), and thereto is added dropwise propionyloxyacetyl chloride (3.0 ml) which is cooled in an ice bath. The mixture is stirred at room temperature for 1 hour, and thereafter, water is added thereto, and the mixture is extracted with methylene chloride. The organic layer is dried over anhydrous sodium sulfate, and the solvent is distilled off under reduced pressure. The resulting crude crystals are recrystallized from ethanol to give the title compound (1.6 g) having the following physical properties.

Melting point: 103°–105° C.

IR (KBr) υ: 3410, 3350, 2980, 2945, 2220, 1745, 1715, 1620, 1575, 1555, 1515, 1485, 1430, 1365, 1315, 1275, 1195, 780 cm$^{-1}$.

NMR (DMSO-d$_6$) δ: 9.69 (1 H, brs), 7.25–6.47 (3 H, m), 5.86 (1 H, brt), 4.64 (2 H, s), 3.18 (2 H, m), 2.42 (2 H, q), 1.14 (3 H, t), 1.06 (3 H, t).

Elementary analysis:
Calcd. (%): C,61.08; H,6.22; N,15.26;
Found (%): C,61.06; H,6.21; N,15.28.

EXAMPLE 12

Preparation of 2-(acetoxyacetylamino)-6-methoxybenzamide:

To a solution of 2-amino-6-methoxybenzamide (1.7 g) in methylene chloride (20 ml) is added pyridine (1.6 ml), and thereto is added dropwise acetoxyacetyl chloride (1.1 ml) which is cooled in an ice bath. The mixture is stirred at room temperature for 2 hours, and thereafter, the solvent is distilled off under reduced pressure. The resulting crude crystals are washed with water and then are recrystallized from ethanol to give the title compound (2.1 g) having the following physical properties.

Melting point: 163°–165° C.

IR (KBr) υ: 3465, 3195, 1750, 1695, 1650, 1605, 1520, 1470, 1440, 1395, 1235, 1095, 1080, 925, 815, 785, 540 cm$^{-1}$.

NMR (DMSO-d$_6$) δ: 11.45 (1 H, brs), 8.05–6.84 (3 H, m), 7.91 (2 H, brs), 4.60 (2 H, s), 3.82 (3 H, s), 2.20 (3 H, s)

Elementary analysis:
Calcd. (%): C,54.13; H,5.30; N,10.52;
Found (%): C,54.19; H,5.36; N,10.57.

EXAMPLE 13

Preparation of 2-(acetoxyacetylamino)-6-methoxybenzonitrile:

To a solution of 2-amino-6-methoxybenzonitrile (3.7 g) in methylene chloride (50 ml) is added pyridine (2.4 ml), and thereto is added dropwise acetoxyacetyl chloride (2.7 ml) which is cooled in an ice bath. The mixture is stirred at room temperature for 1 hour, and thereafter, the solvent is distilled off under reduced pressure. The resulting crude crystals are washed with water and ether and then are recrystallized from ethanol to give the title compound (5.4 g) having the following physical properties.

Melting point: 131°–132° C.

IR (KBr) υ: 3435, 3210, 3095, 3070, 2220, 1775, 1695, 1610, 1590, 1555, 1485, 1460, 1440, 1425, 1390, 1380, 1305, 1275, 1245, 1220, 1100, 970, 845, 795, 740, 725 cm$^{-1}$.

NMR (DMSO-d$_6$) δ: 9.94 (1 H, brs), 7.54–6.96 (3 H, m), 4.65 (2 H, s), 3.85 (3 H, s), 2.10 (3 H, s).

Elementary analysis:
Calcd. (%): C,58.06; H,4.87; N,11.28;
Found (%): C,58.02; H,4.92; N,11.29.

EXAMPLE 14

Preparation of 2-(hydroxyacetylamino)-6-(methylamino)benzonitrile:

To a solution of 2-(acetoxyacetylamino)-6-(methylamino)benzonitrile (2 g) in methanol (250 ml) is added dropwise 28% aqueous ammonia (5.5 ml). The mixture is stirred at room temperature for 30 minutes, and thereafter, the solvent is distilled off under reduced pressure. The resulting crude crystals are recrystallized from ethanoltoluene to give the title compound (1.4 g) having the following physical properties.

Melting point: 160°–162° C.

IR (KBr) υ: 3415, 3345, 2920, 2305, 1675, 1615, 1575, 1560, 1505, 1435, 1420, 1335, 1305, 1185, 1070, 790, 675 cm$^{-1}$.

NMR (DMSO-d$_6$) δ: 9.25 (1 H, brs), 7.23–6.36 (3 H, m), 6.06 (1 H, brq), 3.95 (2 H, s), 2.72 (3 H, d).

Elementary analysis:
Calcd. (%): C,58.53; H,5.40; N,20.48;
Found (%): C,58.28; H,5.47; N,20.43.

EXAMPLE 15

Preparation of 2-(ethylamino)-6-(hydroxyacetylamino)benzonitrile:

To a solution of 2-(acetoxyacetylamino)-6-(ethylamino)benzonitrile (4.5 g) in methanol (250 ml) is added dropwise 28% aqueous ammonia (5.5 ml). The mixture is stirred at room temperature for 1 hour, and thereafter, the solvent is distilled off under reduced pressure. The resulting crude crystals are recrystallized from ethanol to give the title compound (2.6 g) having the following physical properties.

Melting point: 111°–112° C.

IR (KBr) υ: 3355, 3320, 2975, 2905, 2210, 1675, 1565, 1515, 1490, 1485, 1330, 1305, 1285, 1160, 1080, 795 cm$^{-1}$.

NMR (DMSO-d6) δ: 9.38 (1 H, brs), 7.19–6.42 (3 H, m), 5.91 (1 H, t), 3.94 (2 H, s), 3.13 (3 H, m), 1.14 (3 H, t)

Elementary analysis:
Calcd. (%): C,60.30; H,5.98; N,19.18;
Found (%): C,60.19; H,6.01; N,19.17.

EXAMPLE 16

Preparation of 2-(acetoxyacetylamino)-6-nitrobenzonitrile:

A solution of 2-amino-6-nitrobenzonitrile (6.5 g) in pyridine (100 ml) is cooled in an ice bath and thereto is added dropwise acetoxyacetyl chloride (4.4 ml). The mixture is stirred at room temperature for 1 hour, and thereafter, pyridine is distilled off under reduced pressure, and then water is added thereto, and the mixture is extracted with methylene chloride. The organic layer is washed with 1N hydrochloric acid and dried over anhydrous sodium sulfate, and the solvent is distilled off under reduced pressure. The resulting crude crystals are recrystallized from ethanol to give the title compound (5.8 g) having the following physical properties.

Melting point: 157°–158° C.

IR (KBr) υ: 3445, 3385, 3115, 2945, 2265, 1765, 1725, 1580, 1535, 1470, 1450, 1380, 1355, 1315, 1295, 1240, 1180, 1065, 925, 910, 815, 755, 655 cm$^{-1}$.

NMR (DMSO-$d_6$) δ: 10.52 (1 H, brs), 8.00 (3 H, m), 4.72 (2 H, s), 2.13 (3 H, s)

Elementary analysis:
Calcd. (%): C,50.20; H,3.46; N,15.96;
Found (%): C,50.18; H,3.48; N,15.91.

EXAMPLE 17

Preparation of 2,6-bis(acetoxyacetylamino)benzonitrile:

To a solution of 2,6-diaminobenzonitrile (9.3 g) in methylene chloride (200 ml) is added pyridine (19.4 ml), and thereto is added dropwise acetoxyacetyl chloride (24 ml) which is cooled in an ice bath. The mixture is stirred at room temperature for 30 minutes, and thereafter, the solvent is distilled off under reduced pressure and thereto is added water. The resulting crude crystals are separated by filtration and are recrystallized from ethanol to give the title compound (18 g) having the following physical properties.

Melting point: 151°–153° C.

IR (KBr) υ: 3455, 3330, 3270, 2225, 1760, 1715, 1690, 1595, 1540, 1480, 1425, 1375, 1285, 1250, 1215, 1180, 1090, 1015, 965, 825, 805, 635, 455 cm$^{-1}$.

NMR (DMSO-$d_6$) δ: 10.25 (2H, brs), 7.50 (3 H, m), 4.66 (4 H, s), 2.11 (6 H, s)

Elementary analysis:
Calcd. (%): C,54.05; H,4.54; N,12.61;
Found (%): C,54.03; H,4.56; N,12.57.

EXAMPLE 18

Preparation of 2-(acetoxyacetylamino)-6-chlorobenzonitrile:

To a solution of 2-amino-6-chlorobenzonitrile (4.6 g) in chloroform (100 ml) is added triethylamine (4.8 ml), and thereto is added dropwise acetoxyacetyl chloride (3.8 ml). The mixture is stirred at room temperature for 1 hour, and thereafter, water is added thereto, and the mixture is extracted with chloroform. The organic layer is washed with saturated aqueous sodium chloride and then dried over anhydrous sodium sulfate, and the solvent is distilled off under reduced pressure. The resulting crude crystals are recrystallized from ethanol-water to give the title compound (3.8 g) having the following physical properties.

Melting point: 109°–110° C.

IR (KBr) υ: 3290, 3110, 2250, 1850, 1700, 1600, 1585, 1540, 1460, 1440, 1430, 1380, 1310, 1285, 1255, 1180, 1155, 1075, 975, 905, 800, 730 cm$^{-1}$.

NMR (DMSO-$d_6$) δ: 10.37 (1 H, brs), 7.80–7.49 (3 H, m), 4.72 (2 H, s), 2.13 (3 H, s)

Elementary analysis:
Calcd. (%): C,52.29; H,3.59; N,11.09; Cl,14.03;
Found (%): C,52.30; H,3.59; N,11.14; Cl,14.07.

EXAMPLE 19

Preparation of 2-(acetoxyacetylamino)-6-aminobenzamide:

To a mixture of 2-(acetoxyacetylamino)-6-nitrobenzonitrile (5.7 g) and ethanol (50 ml) are added cyclohexene (10.5 ml) and 10% palladium-carbon (4.7 g). The mixture is refluxed for 20 minutes, and the reaction mixture is cooled to room temperature, and the solid materials are filtered off. The filtrate is distilled under reduced pressure. The residual crude crystals are recrystallized from ethanol to give the title compound (1.2 g) having the following physical properties.

Melting point: 181°–184° C.

IR (KBr) υ: 3505, 3445, 3385, 3205, 1775, 1735, 1660, 1615, 1575, 1475, 1395, 1300, 1245, 1075, 970, 930, 810, 790, 695 cm$^{-1}$.

NMR (DMSO-$d_6$) δ: 10.00 (1 H, brs), 7.53 (2 H, brs), 7.03–6.44 (3 H, m), 5.26 (2 H, brs), 4.51 (2 H, s), 2.14 (3 H, s).

Elementary analysis:
Calcd. (%): C,52.59; H,5.21; N,16.73;
Found (%): C,52.57; H,5.22; N,16.64.

EXAMPLE 20

Preparation of 2-(acetoxyacetylamino)-6-(diethylamino)benzonitrile:

To a solution of 2-amino-6-(diethylamino)benzonitrile (3 g) in methylene chloride (50 ml) is added pyridine (1.4 ml), and thereto is added dropwise acetoxyacetyl chloride (1.8 ml) which is cooled in an ice bath. The mixture is stirred at room temperature for 1 hour, and thereafter, water is added thereto, and the mixture is extracted with methylene chloride. The organic layer is dried over anhydrous sodium sulfate, and the solvent is distilled off under reduced pressure. The resulting residue is recrystallized from hexane to give the title compound (1.1 g) having the following physical properties.

Melting point: 50°–51° C.

IR (KBr) υ: 3445, 3385, 2975, 2935, 2190, 1750, 1720, 1610, 1570, 1500, 1475, 1380, 1350, 1320, 1270, 1240, 1160, 1060, 925, 785, 660 cm$^{-1}$.

NMR (DMSO-$d_6$) δ: 9.91 (1 H, brs), 7.11 (3 H, m), 4.66 (2 H, s), 3.29 (4 H, q), 2.12 (3 H, s), 1.08 (6 H, t)

Elementary analysis
Calcd. (%): C,62.27; H,6.62; N,14.52;
Found (%): C,62.18; H,6.63; N,14.51.

EXAMPLE 21

Preparation of 2-(acetoxyacetylamino)-6-piperidinobenzonitrile:

To a solution of 2-amino-6-piperidinobenzonitrile (8.8 g) in methylene chloride (100 ml) is added pyridine (3.3 ml), and thereto is added dropwise acetoxyacetyl chloride (4.3 ml) which is cooled in an ice bath. The mixture is stirred at room temperature for 1 hour, and thereafter, water is added thereto, and the mixture is extracted with methylene chloride. The organic layer is dried over anhydrous sodium sulfate, and the solvent is distilled off under reduced pressure. The resulting crude crystals are recrystallized from ethyl acetate-hexane to give the title compound (3.2 g) having the following physical properties.

Melting point: 90°–92° C.

IR (KBr) υ: 3410, 3275, 2945, 2835, 2220, 1755, 1695, 1605, 1575, 1550, 1480, 1470, 1445, 1425, 1385, 1285, 1250, 1225, 1205, 1085, 1070, 960 cm$^{-1}$.

NMR (DMSO-$d_6$) δ: 9.99 (1 H, brs), 7.60–6.85 (3 H, m), 4.68 (2 H, s), 3.08 (4 H, m), 1.62 (6 H, m)

Elementary analysis:
Calcd. (%): C,63.99; H,6.04; N,13.99;
Found (%): C,63.77; H,6.34; N,13.89.

EXAMPLE 22

Preparation of 2-(acetoxyacetylamino)-6-(N-ethyl-N-methylamino)benzonitrile:

To a solution of 2-amino-6-(N-ethyl-N-methylamino)-benzonitrile (4 g) in methylene chloride (200 ml) is added pyridine (2.4 ml), and thereto is added dropwise acetoxyacetyl chloride (3.3 ml) which is cooled in an ice bath. The mixture is stirred at room temperature for 1 hour, and thereafter, water is added thereto, and the mixture is extracted with methylene chloride. The organic layer is dried over anhydrous sodium sulfate, and the solvent is distilled off under reduced pressure. The resulting residue is recrystallized from hexane to give the title compound (4.2 g) having the following physical properties.

Melting point: 57°–58° C.

IR (KBr) $v$: 3445, 3405, 3225, 3060, 2980, 2215, 1755, 1690, 1605, 1575, 1555, 1485, 1425, 1375, 1275, 1250, 1220, 1080, 1070, 805 cm$^{-1}$.

NMR (DMSO-d$_6$) δ: 9.95 (1 H, brs), 7.06 (3 H, m), 4.66 (2 H, s), 3.28 (3 H, q), 2.85 (2 H, s), 2.12 (3 H, s), 1.15 (3 H, t).

Elementary analysis:
Calcd. (%): C,61.08; H,6.22; N,15.26;
Found (%) C,61.02; H,6.19; N,15.23.

EXAMPLE 23

Preparation of 2-(hydroxyacetylamino)-6-piperidinobenzonitrile:

To a solution of 2-(acetoxyacetylamino)-6-piperidino)benzonitrile (3 g) in methanol (100 ml) is added dropwise 28% aqueous ammonia (10 ml). The mixture is stirred at room temperature for 1 hour, and thereafter, the solvent is distilled off under reduced pressure. The resulting residue is recrystallized from toluene-hexane to give the title compound (1.4 g) having the following physical properties.

Melting point: 121°–124° C.

IR (KBr) $v$: 3410, 3345, 2975, 2850, 2825, 2210, 1705, 1660, 1605, 1585, 1550, 1485, 1440, 1395, 1340, 1305, 1255, 1125, 1080, 1005, 985, 855, 800 cm$^{-1}$.

NMR (DMSO-d$_6$) δ: 9.55 (1 H, brs), 7.61–6.80 (3 H, m), 6.07 (1 H, t), 4.01 (2 H, d), 3.07 (4 H, m), 1.60 (6 H, m)

Elementary analysis:
Calcd. (%): C,64.85; H,6.61; N,16.21;
Found: C,64.89; H,6.62; N,16.24.

EXAMPLE 24

Preparation of 2-(acetoxyacetylamino)-6-morpholinobenzonitrile:

To a solution of 2-amino-6-morpholinobenzonitrile (5.6 g) in pyridine (15 ml) is added dropwise acetoxyacetyl chloride (3.3 ml) which is cooled in an ice bath. The mixture is stirred at room temperature for 1 hour, and thereafter, pyridine is distilled off under reduced pressure and thereto is added water, and the mixture is extracted with methylene chloride. The organic layer is dried over anhydrous sodium sulfate, and the solvent is distilled off under reduced pressure. The resulting residue is recrystallized from ethanol-toluene-water to give the title compound (4.7 g) having the following physical properties.

Melting point: 131°–132° C.

IR (KBr) $v$: 3475, 3395, 2955, 2855, 2205, 1735, 1705, 1600, 1575, 1550, 1480, 1375, 1305, 1240, 1225, 1120, 1060, 1025, 875, 805, 650 cm$^{-1}$.

NMR (DMSO-d$_6$) δ: 10.07 (1 H, brs), 7.26 (3 H, m), 4.68 (2 H, s), 3.72 (4 H, m), 3.08 (4 H, m), 2.13 (3 H, s).

Elementary analysis:
Calcd. (%): C,59.40; H,5.65; N,13.85;
Found (%): C,59.31; H,5.60; N,13.89.

EXAMPLE 25

Preparation of 2,6-bis(hydroxyacetylamino)benzonitrile:

To a solution of 2,6-bis(acetoxyacetylamino)benzonitrile (6.7 g) in methanol (700 ml) is added dropwise 28% aqueous ammonia (10 ml). The mixture is stirred at room temperature for 1 hour, and thereafter, the solvent is distilled off under reduced pressure. The resulting crude crystals are recrystallized from ethanol to give the title compound (3.8 g) having the following physical properties.

Melting point: 188°–189° C.

IR (KBr) $v$: 3445, 3395, 3355, 2225, 2210, 1715, 1690, 1595, 1525, 1485, 1445, 1360, 1305, 1280, 1215, 1175, 1100 1085, 1070, 810, 670 cm$^{-1}$.

NMR (DMSO-d$_6$) δ: 9.60 (2H, brs), 7.61 (3 H, s), 6.12 (2 H, brs), 4.02 (4 H, s)

Elementary analysis:
Calcd. (%): C,53.01; H,4.45; N,16.86;
Found (%): C,52.69; H,4.45; N,16.85.

EXAMPLE 26

Preparation of 2-(hydroxyacetylamino)-6-methoxybenzonitrile:

To a solution of 2-(acetoxyacetylamino)-6-methoxybenzonitrile (2.5 g) in methanol (250 ml) is added dropwise 28%aqueous ammonia (5 ml). The mixture is stirred at room temperature for 1 hour, and thereafter, the solvent is distilled off under reduced pressure. The resulting crude crystals are recrystallized from ethanol to give the title compound (1.8 g) having the following physical properties.

Melting point: 144°–145° C.

IR (KBr) $v$: 3580, 3340, 2980, 2205, 1695, 1610, 1595, 1555, 1515, 1495, 1445, 1360, 1300, 1280, 1195, 1105, 1075, 990, 890 cm$^{-1}$.

NMR (DMSO-d$_6$) δ: 9.57 (1 H, brs), 7.62 (2 H, m), 6.99 (1 H, m), 6.06 (1 H, brs), 4.03 (2 H, s), 3.90 (3 H, s).

Elementary analysis:
Calcd. (%): C,58.25; H,4.88; N,13.58;
Found (%): C,58.03; H,4.91; N,13.59.

EXAMPLE 27

Preparation of 2-(hydroxyacetylamino)-6-morpholinobenzonitrile:

To a solution of 2-(acetoxyacetylamino)-6-morpholinobenzonitrile (3 g) in methanol (200 ml) is added dropwise 28% aqueous ammonia (10 ml). The mixture is stirred at room temperature for 1 hour, and thereafter, the solvent is distilled off under reduced pressure. The resulting residue is recrystallized from ethanol-water to give the title compound (1.4 g) having the following physical properties.

Melting point: 123°–126° C.

IR (KBr) $v$: 3440, 3340, 2860, 2220, 1675, 1600, 1580, 1545, 1480, 1445, 1300, 1275, 1250, 1120, 1080, 1020, 810 cm$^{-1}$.

NMR (DMSO-d$_6$) δ: 9.60 (1 H, brs), 7.60–6.85 (3 H, m), 6.08 (1 H, t), 4.02 (2 H, d), 3.23 (4 H, m), 3.11 (4 H, m)

Elementary analysis:
Calcd. (%): C,59.76; H,5.79; N,16.08;

Found (%): C,59.84; H,5.78; N,16.15.

What is claimed is:

1. A substituted acetamide compound of the formula:

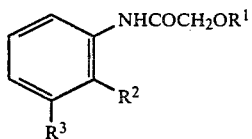

wherein $R^1$ is hydrogen atom, a lower alkyl group, a lower acyl group, or an aryl group; $R^2$ is cyano group or aminocarbonyl group; $R^3$ is a halogen atom, nitro group, a lower alkoxy group, a group of the formula: $-NR^4R^5$ (wherein $R^4$ is hydrogen atom, a lower alkyl group or a group of the formula: $-COCH_2OR^1$; $R^5$ is hydrogen atom or a lower alkyl group), or pharmaceutically acceptable acid addition salt thereof.

2. The compound according to claim 1, wherein $R^1$ is hydrogen atom, an alkyl group having 1 to 6 carbon atoms, an acyl group having 1 to 6 carbon atoms; $R^2$ is cyano group or aminocarbonyl group; $R^3$ is halogen atom, nitro group, an alkoxy group having 1 to 6 carbon atoms, a group of the formula: $-NR^4R^5$ (wherein $R^4$ is hydrogen atom, an alkyl group having 1 to 6 carbon atoms, a hydroxyacetyl group, an acyloxyacetyl group, an alkoxyacetyl group; and $R^5$ is hydrogen atom or an alkyl group having 1 to 6 carbon atoms).

3. The compound according to claim 1, wherein $R^1$ is hydrogen atom, methyl, ethyl, acetyl, or propionyl; $R^2$ is cyano group or aminocarbonyl group; $R^3$ is chlorine atom, methoxy group, mono- or dimethylamino group, mono- or diethylamino group, hydroxyacetylamino group, or acetoxyacetylamino group.

4. The compound according to claim 1 which is a member selected from the following compounds:

2-(Acetoxyacetylamino)-6-(ethylamino)benzonitrile,
2-(Ethylamino)-6-(methoxyacetylamino)benzonitrile,
2-(Methoxyacetylamino)-6-(methylamino)benzonitrile,
2-(Acetoxyacetylamino)-6-(methylamino)benzonitrile,
2-(Ethoxyacetylamino)-6-(methylamino)benzonitrile,
2-(Ethoxyacetylamino)-6-(ethylamino)benzonitrile,
2-(Acetoxyacetylamino)-6-(N-acetoxyacetyl-N-methylamino)benzonitrile,
2-(Methylamino)-6-(phenoxyacetylamino)benzonitrile,
2-(Acetoxyacetylamino)-6-(ethylamino)benzamide,
2-(Acetoxyacetylamino)-6-(methylamino)benzamide,
2-(Ethylamino)-6-(propionyloxyacetylamino)benzonitrile,
2-(Acetoxyacetylamino)-6-methoxybenzamide,
2-(Acetoxyacetylamino)-6-methoxybenzonitrile,
2-(Hydroxyacetylamino)-6-(methylamino)benzonitrile,
2-(Ethylamino)-6-(hydroxyacetylamino)benzonitrile,
2-(Acetoxyacetylamino)-6-nitrobenzonitrile,
2,6-Bis(acetoxyacetylamino)benzonitrile,
2-(Acetoxyacetylamino)-6-chlorobenzonitrile,
2-(Acetoxyacetylamino)-6-aminobenzamide,
2-(Acetoxyacetylamino)-6-(diethylamino)benzonitrile,
2-(Acetoxyacetylamino)-6-(N-ethyl-N-methylamino)benzonitrile,
2,6-Bis(hydroxyacetylamino)benzonitrile,
2-(Hydroxyacetylamino)-6-methoxybenzonitrile 5. A pharmaceutical composition for the prophylaxis and treatment of allergic diseases, which comprises as an active ingredient a pharmaceutically effective amount of a substituted acetamide compound as set forth in claim 1 in admixture with a pharmaceutical carrier or diluent.

* * * * *